US00PP37063P2

(12) United States Plant Patent
Miyazaki

(10) Patent No.: US PP37,063 P2
(45) Date of Patent: Oct. 21, 2025

(54) ***SENECIO* PLANT NAMED 'Sene Isifuro'**

(50) Latin Name: *Senecio cruentus*
Varietal Denomination: Sene Isifuro

(71) Applicant: Kiyoshi Miyazaki, Shiga (JP)

(72) Inventor: Kiyoshi Miyazaki, Shiga (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 18/897,672

(22) Filed: Sep. 26, 2024

(51) Int. Cl.
*A01H 5/02* (2018.01)
*A01H 6/14* (2018.01)

(52) U.S. Cl.
USPC ..... Plt./480

(58) Field of Classification Search
USPC ..... Plt./480
CPC ..... A01H 5/02; A01H 5/00; A01H 6/14
See application file for complete search history.

(56) References Cited

PUBLICATIONS

California Spring Trials—Garden Center 2024 retrieved on Jan. 13, 2025 at https://www.gardencentermag.com/page/cast-california-spring-trials/, 6 pp. (Year: 2024).*
Garden Center 2024 California Spring Trials Preview: Suntory Flowers retrieved on Jan. 13, 2025 at https://www.gardencentermag.com/page/suntory-flowers-california-spring-trials/, 9 pp. (Year: 2024).*
Suntory Flowers 2025 Catalog retrieved on Jan. 13, 2025 at https://suntoryflowers.com/wp-content/uploads/2024/02/2025-Suntory-Flowers-Catalog.pdf, pp. 1-3,32-34. (Year: 2025).*

* cited by examiner

*Primary Examiner* — June Hwu
(74) *Attorney, Agent, or Firm* — C. Anne Whealy

(57) ABSTRACT

A new and distinct cultivar of *Senecio* plant named 'Sene Isifuro', characterized by its compact, upright and uniformly mounded plant habit; vigorous growth habit; freely branching habit; freely flowering habit; daisy-type inflorescences with spoon-shaped ray florets with dark violet-colored upper surfaces and light violet-colored lower surfaces; and good garden performance.

2 Drawing Sheets

Figure 1:
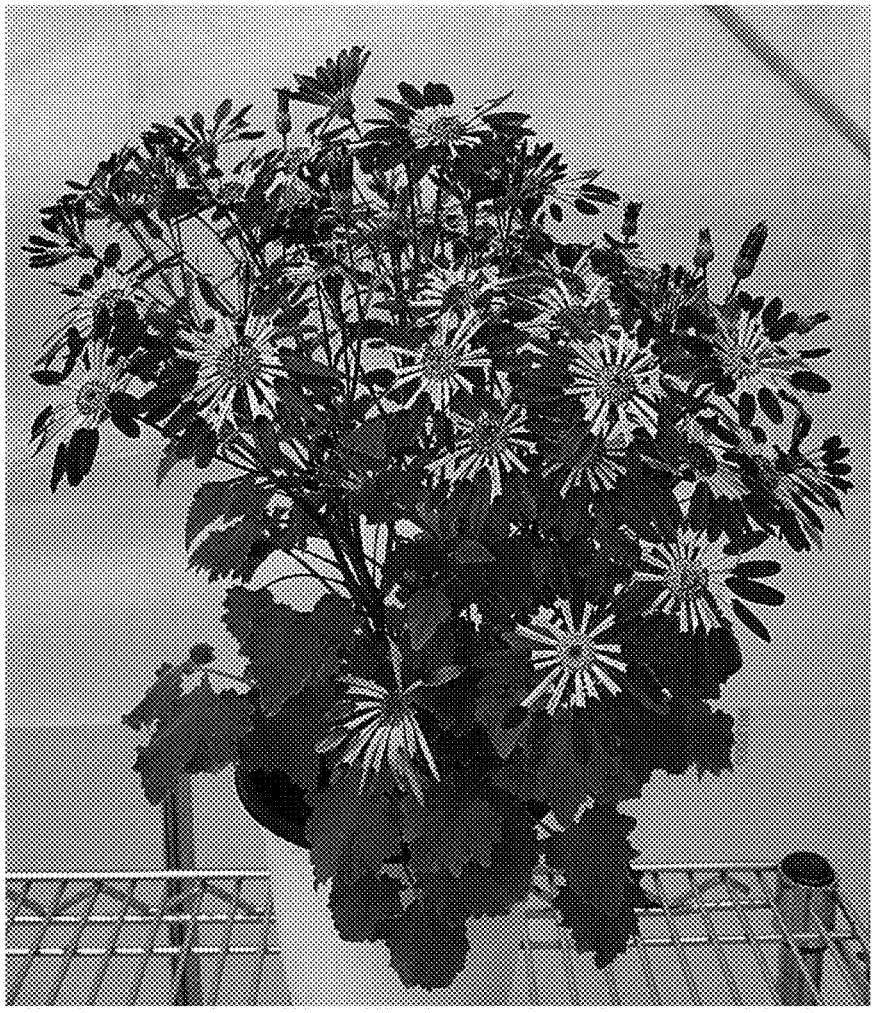

Botanical designation: *Senecio cruentus.*
Cultivar denomination: 'SENE ISIFURO'.

BACKGROUND OF THE INVENTION

The present invention relates to a new and distinct cultivar of *Senecio* plant, botanically known as *Senecio cruentus*, commonly known as Cineraria, and hereinafter referred to by the name 'Sene Isifuro'.

The new *Senecio* plant is a product of a planned breeding program conducted by the Inventor in Higashiomi, Shiga, Japan. The objective of the breeding program is to create new compact, upright and uniformly mounding *Senecio* plants with a freely-branching habit and numerous unique and attractive inflorescences.

The new *Senecio* plant originated from a cross-pollination conducted by the Inventor in March 2013 of a proprietary selection of *Senecio cruentus* identified as code designation S12-61-3, not patented, as the female, or seed, parent with a proprietary selection of *Senecio cruentus* identified as code designation S12-100-2, not patented, as the male, or pollen, parent. The new *Senecio* plant was discovered and selected by the Inventor as a single flowering plant within the progeny of the stated cross-pollination in a controlled greenhouse environment in Higashiomi, Shiga, Japan in February 2016.

Asexual reproduction of the new *Senecio* plant by terminal vegetative cuttings in a controlled greenhouse environment in Higashiomi, Shiga, Japan since October 2018 has shown that the unique features of this new *Senecio* plant are stable and reproduced true to type in successive generations.

SUMMARY OF THE INVENTION

Plants of the new *Senecio* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sene Isifuro'. These characteristics in combination distinguish 'Sene Isifuro' as a new and distinct *Senecio* plant:

1. Compact, upright and uniformly mounded plant habit.
2. Vigorous growth habit.
3. Freely branching habit.
4. Freely flowering habit.
5. Daisy-type inflorescences with spoon-shaped ray florets with dark violet-colored upper surfaces and light violet-colored lower surfaces.
6. Good garden performance.

Plants of the new *Senecio* can be compared to plants of the female parent selection. Plants of the new *Senecio* differ primarily from plants of the female parent selection in ray floret shape as ray florets of plants of the new *Senecio* are consistently large spoon-shaped whereas ray florets of plants of the female parent selection are small spoon-shaped to close to quilled-shaped.

Plants of the new *Senecio* can be compared to plants of the male parent selection. Plants of the new *Senecio* differ primarily from plants of the male parent selection in ray floret shape as ray florets of plants of the new *Senecio* are consistently spoon-shaped whereas ray florets of plants of the male parent selection are inconsistently spoon-shaped. In addition, upper surfaces of ray florets of plants of the new *Senecio* are darker violet in color than upper surfaces of ray florets of plants of the male parent selection.

Plants of the new *Senecio* can also be compared to plants of *Senecio cruentus* 'Sunsenedibu', disclosed in U.S. Plant Pat. No. 12,181. In side-by-side comparisons, plants of the new *Senecio* differ from plants of 'Sunsenedibu' in the following characteristics:

1. Plants of the new *Senecio* have longer internodes than plants of 'Sunsenedibu'.
2. Plants of the new *Senecio* have smaller leaves than plants of 'Sunsenedibu'.
3. Inflorescences of plants of the new *Senecio* have more ray florets than inflorescences of plants of 'Sunsenedibu'.
4. Ray florets of plants of the new *Senecio* are spoon-shaped whereas ray florets of plants of 'Sunsenedibu' are flat and ligulate in shape.
5. Plants of the new *Senecio* have longer and thicker peduncles than plants of 'Sunsenedibu'.

BRIEF DESCRIPTION OF THE PHOTOGRAPHS

The accompanying photographs illustrate the overall appearance of the new *Senecio* plant showing the colors as true as it is reasonably possible to obtain in colored reproductions of this type. Colors in the photographs may differ slightly from the color values cited in the detailed botanical description which accurately describe the colors of the new *Senecio* plant.

The photograph on the first photographic sheet (FIG. 1) is a side perspective view of a typical flowering plant of 'Sene Isifuro' grown in a container.

Figure 2:
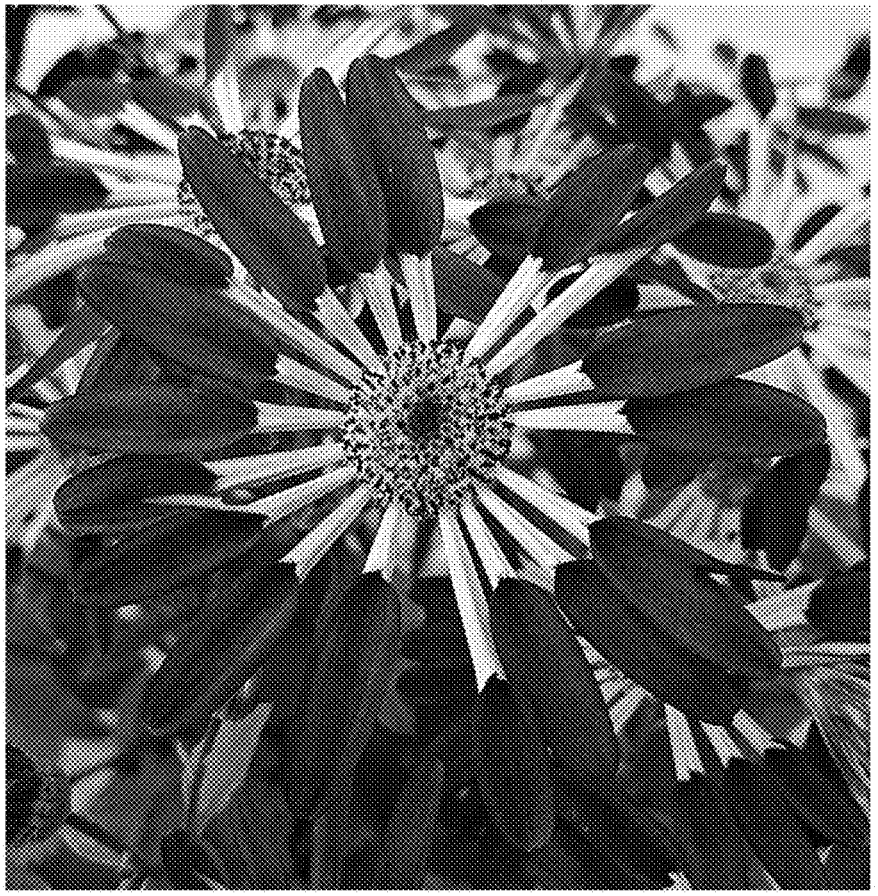

The photograph on the second photographic sheet (FIG. 2) is a close-up view of a typical flowering plant of 'Sene Isifuro'.

DETAILED BOTANICAL DESCRIPTION

The aforementioned photographs, following observations and measurements describe plants grown during the late winter/early spring in 24-cm containers in an outdoor nursery in Higashiomi, Shiga, Japan and under cultural practices typical of commercial *Senecio* production. During the production of the plants, day temperatures averaged 10° C. and night temperatures averaged 5° C. Measurements and numerical values represent averages for typical flowering plants. Plants were six months old when the photographs and the detailed description were taken. In the following description, color references are made to The Royal Horticultural Society Colour Chart, 2015 Edition, except where general terms of ordinary dictionary significance are used.

Botanical classification: *Senecio cruentus* 'Sene Isifuro'.

Parentage:

*Female, or seed, parent*.—Proprietary selection of *Senecio cruentus* identified as code designation S12-61-3, not patented.

*Male, or pollen, parent*.—Proprietary selection of *Senecio cruentus* identified as code designation S12-100-2, not patented.

Propagation:

*Type*.—Terminal vegetative cuttings.

*Time to initiate roots, summer and winter*.—About one week at temperatures about 18° C. to 20° C.

*Time to produce a rooted young plant, summer and winter*.—About four weeks at temperatures about 18° C. to 20° C.

*Root description*.—Fine, fibrous; typically white in color; actual color of the roots is dependent on substrate composition, water quality, fertilizer type and formulation, substrate temperature and physiological age of roots.

*Rooting habit*.—Freely branching, dense.

Plant description:

*Plant form and growth habit*.—Compact, upright and uniformly mounded plant habit; daisy-type inflorescences positioned above the foliar plane with spoon-shaped ray florets; vigorous growth habit; freely branching habit with about four primary branches each with numerous secondary branches.

*Plant height*.—About 34.8 cm.

*Plant diameter*.—About 36.8 cm.

*Lateral branches*.—Length: About 16.4 cm. Diameter: About 3.4 mm. Internode length: About 2.9 cm. Strength: Strong. Aspect: Upright to slightly outwardly. Texture: Sparsely pubescent. Color: Close to 138B.

*Leaf description*.—Arrangement: Alternate, simple. Length: About 5.7 cm. Width: About 6.6 cm. Shape: Cordate. Apex: Obtuse. Base: Cordate. Margin: Serrate with shallow indentations; slightly undulate. Texture, upper surface: Sparsely pubescent. Texture, lower surface: Densely pubescent. Venation pattern: Pinnate; reticulate. Color: Developing leaves, upper surface: Close to 137B. Developing leaves, lower surface: Close to 190A. Fully expanded leaves, upper surface: Close to 137B; venation, close to 138A. Fully expanded leaves, lower surface: Close to 191B; venation, close to 191A. Leaf petioles: Length: About 7.5 cm. Diameter: About 1.9 mm. Texture, upper and lower surfaces: Pubescent. Color, upper and lower surfaces: Close to 137B.

Inflorescence description:

*Appearance*.—Daisy-type inflorescences with spoon-shaped ray florets; inflorescences arising from upper leaf axils and positioned above the foliar plane on strong peduncles; disc and ray florets developing acropetally on a capitulum; inflorescences face mostly upright to outwardly; freely flowering habit with about five inflorescences per lateral branch and about 64 inflorescences developing per plant during the flowering season.

*Fragrance*.—Moderate, pleasant.

*Natural flowering season*.—Plants of the new *Senecio* begin flowering about 22 weeks after planting; plants flower continuously from winter to late spring in Japan; depending on temperature, inflorescences maintain good substance for several weeks on the plant; inflorescences persistent.

*Inflorescence buds*.—Height: About 1.9 cm. Diameter: About 7.2 mm. Shape: Globose. Color: Close to 93C.

*Inflorescence size*.—Diameter: About 6.1 cm. Depth (height): About 1.2 cm. Disc diameter: About 1.1 cm.

*Receptacles*.—Diameter: About 6 mm. Height: About 1.3 mm. Color: Close to 145B.

*Ray florets*.—Quantity and arrangement: About 17 per inflorescence arranged in a single whorl. Length: About 2.7 cm. Width: Distally (open section), about 7 mm and proximally (fused section), about 1 mm to 2 mm. Shape: Spoon-shaped. Apex: Rounded acute; occasionally, emarginate. Base: Fused into a narrow elongated tube. Margin: Entire, not undulate. Aspect: Initially upright, then horizontal; flat. Texture, upper and lower surfaces: Smooth, glabrous. Color: When opening, upper surface: Distally (open section), close to N89B and proximally (fused section), close to 92C. When opening, lower surface: Close to 92C. Fully opened, upper surface: Distally (open section), close to N89C and proximally (fused section), close to 92B and 92D; venation, similar to lamina colors; open section color becoming closer to 92A with subsequent development and fused section color does not change with subsequent development. Fully opened, lower surface: Close to 92B and 92D; venation, close to 92B and 92D; color does not change with subsequent development.

*Disc florets*.—Quantity per inflorescence: About 133. Length: About 7.1 mm. Diameter, distally: About 1.6 mm. Diameter, proximally: About 0.6 mm. Shape: Tubular; apex dentate, five-pointed. Texture: Smooth, glabrous. Color, immature: Initially, close to 93A and becoming closer to 92A with development. Color, mature: Close to 92C.

*Phyllaries*.—Quantity and arrangement: About 22 per inflorescence arranged in a single whorl forming a cylindrical involucre. Length: About 2.5 mm. Width: About 1.3 mm. Shape: Lanceolate; slightly recurved. Apex: Narrowly acute. Base: Fused. Margin: Entire. Texture, upper and lower surfaces: Smooth, glabrous. Color, inner and outer surfaces: Close to 138A.

*Peduncles*.—Length, terminal peduncle: About 4.1 mm. Diameter: About 1.4 mm. Strength: Strong. Aspect: Upright to slightly outwardly. Texture: Smooth, glabrous. Color: Close to 138A.

*Reproductive organs*.—Androecium: Present on disc florets only. Filament length: About 1.2 mm. Filament color: Close to 145D. Anther size: About 0.2 mm by 1.2 mm. Anther shape: Narrowly ellipsoidal. Anther color: Close to N77A. Pollen amount: Moderate. Pollen color: Close to 7A. Gynoecium: Present on both ray and disc florets. Pistil length: About 6.5 mm. Stigma shape: Bi-parted. Stigma color: Close to N92B. Style color: Close to 157D. Ovary color: Close to 145C.

*Seeds and fruits*.—To date, seed and fruit development have not been observed on plants of the new *Senecio*.

Pathogen & pest resistance: To date, plants of the new *Senecio* have not been observed to be resistant to pathogens and pests common to *Senecio* plants.

Garden performance & temperature tolerance: Plants of the new *Senecio* have good garden performance and have been observed to tolerate temperatures ranging from about 0° C. to about 30° C.

It is claimed:

1. A new and distinct *Senecio* plant named 'Sene Isifuro' as herein illustrated and described.

* * * * *